: US006132374A

United States Patent [19]
Hossack et al.

[11] Patent Number: 6,132,374
[45] Date of Patent: Oct. 17, 2000

[54] ULTRASONIC IMAGING METHOD AND SYSTEM

[75] Inventors: John A. Hossack, Palo Alto; Ching-Hua Chou, Fremont, both of Calif.

[73] Assignee: Acuson Corporation, Mountain View, Calif.

[21] Appl. No.: 08/904,825

[22] Filed: Aug. 1, 1997

[51] Int. Cl.[7] ........................................ A61B 8/00
[52] U.S. Cl. ............................................... 600/443
[58] Field of Search .................................. 600/443, 447, 600/454, 438, 442, 458; 128/916

[56] References Cited

U.S. PATENT DOCUMENTS

| | | |
|---|---|---|
| Re. 34,566 | 3/1994 | Ledley . |
| Re. 35,148 | 1/1996 | Lizzi et al. . |
| 3,617,994 | 11/1971 | Glenn et al. . |
| 3,640,271 | 2/1972 | Horton . |
| 3,771,116 | 11/1973 | Farrah . |
| 4,290,310 | 9/1981 | Anderson . |
| 4,322,974 | 4/1982 | Abele et al. . |
| 4,445,379 | 5/1984 | Yamaguchi et al. . |
| 4,475,397 | 10/1984 | Riley et al. . |
| 4,534,221 | 8/1985 | Fife et al. . |
| 4,662,222 | 5/1987 | Johnson . |
| 4,694,699 | 9/1987 | Cheeke . |
| 4,712,037 | 12/1987 | Verbeek et al. . |
| 4,783,839 | 11/1988 | Bamber . |
| 4,803,994 | 2/1989 | Burke . |
| 4,872,346 | 10/1989 | Kelly-Fry et al. . |
| 4,913,157 | 4/1990 | Pratt, Jr. et al. . |
| 5,111,823 | 5/1992 | Cohen . |
| 5,111,824 | 5/1992 | Lazenby et al. . |
| 5,115,809 | 5/1992 | Saitoh et al. . |
| 5,135,000 | 8/1992 | Akselrod et al. . |
| 5,158,071 | 10/1992 | Umemura et al. . |
| 5,187,687 | 2/1993 | Burckhardt et al. . |
| 5,195,520 | 3/1993 | Schlief et al. . |
| 5,197,477 | 3/1993 | Peterson et al. . |
| 5,233,994 | 8/1993 | Shmulewitz . |
| 5,255,683 | 10/1993 | Monaghan . |
| 5,259,384 | 11/1993 | Kaufman et al. . |
| 5,287,753 | 2/1994 | Routh et al. . |
| 5,313,948 | 5/1994 | Murashita et al. . |
| 5,357,964 | 10/1994 | Spivey et al. . |
| 5,358,466 | 10/1994 | Aida et al. . |
| 5,379,642 | 1/1995 | Reckwerdt et al. . |
| 5,379,770 | 1/1995 | Van Veen . |
| 5,386,830 | 2/1995 | Powers et al. . |
| 5,396,285 | 3/1995 | Hedberg et al. . |
| 5,409,688 | 4/1995 | Quay . |

(List continued on next page.)

FOREIGN PATENT DOCUMENTS

| | | |
|---|---|---|
| 0 357 164 | of 0000 | European Pat. Off. . |
| 0 770 352 A1 | 5/1997 | European Pat. Off. . |
| 0851241 A2 | 7/1998 | European Pat. Off. . |
| 890072 | 12/1981 | Russian Federation . |
| WO 98/20361 | 5/1998 | WIPO . |

OTHER PUBLICATIONS

John G. Abbott et al., "Acoustic Speckle: Theory and Experimental Analysis", *Ulatrason. Imaging*, vol. 1, pp. 303–374, 1979.

(List continued on next page.)

*Primary Examiner*—Marvin M. Lateef
*Assistant Examiner*—Maulin Patel
*Attorney, Agent, or Firm*—Brinks Hofer Gilson & Lione

[57] ABSTRACT

An ultrasonic imaging system and method provide a composite image having a near-field region and a far-field region that are displayed in a common imaging mode. The near-field region emphasizes received ultrasonic imaging at a harmonic of the fundamental of the transmit waveform, while the far-field region emphasizes received ultrasonic information at the fundamental frequency. In this way the advantages of harmonic imaging are obtained in the near-field without sacrificing penetration performance in the far-field.

41 Claims, 4 Drawing Sheets

U.S. PATENT DOCUMENTS

| | | |
|---|---|---|
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |
| 5,433,204 | 7/1995 | Olson . |
| 5,433,207 | 7/1995 | Pretlow, III . |
| 5,435,311 | 7/1995 | Umemura et al. . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,462,057 | 10/1995 | Hunt et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,526,816 | 6/1996 | Arditi . |
| 5,540,909 | 7/1996 | Schutt . |
| 5,558,092 | 9/1996 | Unger et al. . |
| 5,560,364 | 10/1996 | Porter . |
| 5,568,813 | 10/1996 | Deitrich et al. . |
| 5,577,505 | 11/1996 | Brock-Fisher et al. . |
| 5,579,768 | 12/1996 | Klesenski . |
| 5,579,770 | 12/1996 | Finger . |
| 5,588,435 | 12/1996 | Weng et al. . |
| 5,600,675 | 2/1997 | Engeler . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |
| 5,667,373 | 9/1997 | Wright et al. . |
| 5,713,356 | 2/1998 | Kruger . |
| 5,724,976 | 3/1998 | Mine et al. . |
| 5,740,128 | 4/1998 | Hossack et al. . |
| 5,879,303 | 3/1999 | Averkiou et al. . |
| 5,897,500 | 4/1999 | Zhao ........................................ 600/443 |
| 5,908,389 | 6/1999 | Roundhill et al. . |

OTHER PUBLICATIONS

J. G. Abbott, "Multi–Scan Processing In A Phased Array Imaging System", *Ultrasonics Symposium Proceedings*, IEEE Cat. #78CH 1344—ISU 1978.

M. Elbaum et al., "A Wavelength Diversity Technique For Reduction Of Speckle Size", *Optics Communications*, vol. 5, No. 3, Jun. 1972.

Marek Elbaum et al., "SNR in photocounting images of rough objects in partially coherent light", *Applied Optics*, vol. 2268, 1976.

Robert Entrekin et al., "Real Time Speckle Reduction in B–Mode Images", *IEEE Ultrasonics Symposium Proceedings*, Sep. 1979.

Gordon S. Kino, Acoustic Imaging for Nondestructive Evaluation, *Proceedings of The IEEE*, vol. 67, No. 4, 1979.

Dennis L. Parker et al., "Analysis of B–Scan Speckle Reduction by Resolution Limited Filtering", *Ultrasonic Imaging* 4, 108–125 1982.

U.S. Provisional application No. 60/032,771, 11/26/11996, Powers et al.

Amir et al, IEEE UFFC, vol. 33, pp. 402–411, 1986.

Magnin et al., Ultrasonic Imaging, vol. 4, No. 3, pp. 267–281, 1982.

T.G. Leighton, "Transient excitation of insonated bubbles." Research Notes.

Eric J. Chen, et al., "Young's Modulus Measurements of Soft Tissues with Application to Elasticity Imaging." IEEE Transactions on Ultrasonics, Ferroelectrics, and Fequency Control, vol. 43, No. 1, Jan. 1996.

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1996.

Marc Gensane, "Bubble population measurements with a parametric array." 1994 Acoustical Society of America, 95 (6) June.

Ken Ishihara et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Shmuel Gottlieb, M.D. et al., "Effect of Pressure on Echocardiographic Videodensity from Sonicated Albumin: An In Vitro Model." J. Ultrasound Med. 14 (1995).

J. W. Norris, "The non–linear oscillation of a radially symmetric bubble in a time periodic pressure field." Dynamics and Stability of Systems, vol. 9, No. 1 (1994).

Michael S. Longuet–Higgins, Resonance in nonlinear bubble oscillations. J. Fluid Mech. (1991) vol. 224.

Chiang C. Mei, et al., "Parametric resonance of a spherical bubble." J. Fluid Mech. (1991) vol. 229.

V.L. Newhouse, et al., "Bubble size measurements using the nonlinear mixing of two frequencies." J. Acoust. Soc. Am. 75 (5), May 1984.

Janet B. Jones–Oliveira, et al., "Transient fluid—solid interaction of submerged spherical shells revisited: Proliferation of frequencies and acoustic radiation effects." Accoustical Society of America, 96(2) Pt. 1, Aug. 1994.

Chandra M. Sehgal, PhD., et al., "Sonographic Enhancement of Renal Cortex by Contrast Media." J. Ultrasound Med, 14 (1995).

"Abstract Session IV Contrast and Ischemia" and "Poster Session A New Technologies". Journal of the American Society of Echocardiography, vol. 8, No. 3, May 1995.

Chandra M. Sehgal, PhD, et al., "Influence of Postprocessing Curves on Contrast—Echographic Imaging: Preliminary Studies." J. Ultrasound Med, 14 (1995).

Deborah J. Rubens, M.D., "Sonoelasticity Imaging of Prostate Cancer: In Vitro Results." Radiology, vol. 995, No. 2, 1995.

Kotaro Sato, et al., "Numerical analysis of a gas bubble near a rigid boundary in an oscillatory pressure field." J. Acoustical Society of America, 95 (5), May 1994.

L.W. Anson et al., "Ultrasonic scattering from spherical shells including viscous and thermal effects." J. Acoustical Society of America, 93 (4), Apr. 1993.

B. Schrope, et al., "Simulated Capillary Blood Flow Measurement Using A Nonlinear Ultrasonic Contrast Agent," Ultrasonic Imaging 14 (1992).

Fred Lee, Jr., M.D., et al., "Sonoelasticity Imaging: Results in in Vitro Tissue Specimens." Radiology, vol. 181, No. 1, 1991.

Kevin J. Parker, PhD, et al., "Sonoelasticity of Organs: Shear Waves Ring a Bell." J. Ultrasound Med., 11 (1992).

William Armstrong, M.D., et al., "American Society of Echocardiography Position Paper on Contrast Echocardiography." draft 1—Jun. 6, 1994.

K.J. Parker, et al., "Tissue Response to Mechanical Vibrations for 'Sonoelasticity Imaging'." Ultrasound in Med. & Biol., vol. 16, No. 3, (1990).

Nico de Jong, "Physical properties and technical aspects of ultrasound contrast agents." (one page).

Robert M. Lerner, et al., "'Sonoelasticity' Images Derived from Ultrasound Signals in Mechanically Vibrated Tissues." Ultrasound in Med. & Biol., vol. 16, No. 3, (1990).

J. Ophir, et al., "Elastography: A Quantitative Method for Imaging the Elasticity of Biological Tissues." Ultrasonics Imaging 13 (1991).

J.A. Hossack et al., "Improving transducer performance using multiple active layers." SPIE vol. 1733 (1992).

Volkmar Uhlendorf, et al., "Nonlinear Acoustical Response of Coated Microbubbles in Diagnostic Ultrasound." 1994 Ultrasonics Symposium.

John A. Hossack, et al., "Improving the Characteristics of a Transducer Using Multiple Piezoelectric Layers." IEEE Transactions on Ultrasonics, Ferroelectrics and Frequency Control, vol. 40, No. 2, Mar. 1993.

H. Edward Karrer, et al., "A Phased Array Acoustic Imaging System for Medical Use." 1980 Ultrasonics Symposium.

"HP Ultrasound Technologies—Viability." About HP Ultrasound Imaging, WWW document, 1997.

Ted Christopher, "Finite Amplitude Distortion–Based Inhomogenous Pulse Echo Ultrasonic Imaging." IEEE Transactions on Ultrasonics, Ferroelectrics, and Frequency Control, vol. 44, No. 1, Jan. 1997.

"Supplement to Journal of the American College of Cardiology" American College of Cardiology, $45^{th}$ Annual Scientific Session, Mar. 24–27, 1996 pp. 21A, 63A, 239–240A.

Yang–Sub Lee, et al., "Time–domain modeling of pulsed finite–amplitude sound beams." 1995 Acoustical Society of America, 97 (2), Feb. 1995.

Michalakis A. Averkiou, et al., "Self–demodulation of amplitude–and frequency–modulated pulses in a thermoviscous fluid." J. Acoustical Society of America, 94 (5), Nov. 1993.

ULTRASONIC IMAGING METHOD AND SYSTEM

BACKGROUND OF THE INVENTION

This invention relates to an ultrasonic method and system that utilize both fundamental and harmonic echo ultrasound information to provide an improved ultrasound image.

In most cases, ultrasound imaging systems create images using a transmit ultrasound beam formed at one frequency and a received ultrasound beam formed at a similar frequency. On occasions, the received beam center frequency is modified to some extent the effect of depth and frequency dependent attenuation.

Recently, systems have been described which form receive beams and images using harmonic frequency signals. In this case, the transmit beamformer forms a transmit beam in a passband centered on a fundamental frequency, and the receive beamformer processes received echo ultrasound information at a passband centered at a harmonic of the fundamental frequency. Such systems can operate with additional non-linear contrast agent as described in Uhlendorf U.S. Pat. No. 5,410,516, or alternately they may operate without additional non-linear contrast agent, relying on tissue generated harmonics, as disclosed in the article entitled "Finite Amplitude Distortion-Based In homogeneous Pulse Echo Ultrasonic Imaging" by Ted Christopher (IEEE Trans UFFC, Vol. 44, No. 1, pp. 125–139, January 1997). Harmonic imaging has been found to provide a superior image quality in terms of detail and contrast characteristics under certain scanning conditions. However, penetration into the tissue is severely degraded, at least in midfrequency transducer probes, due to the fact that harmonic signals are formed from only a fraction of the transmitted power, and higher frequency signals are more severely attenuated by body tissues.

SUMMARY OF THE INVENTION

This invention is defined by the following claims, and nothing in this section should be taken as a limitation on the claims. However, by way of introduction it can be said that the preferred embodiments described below create a composite image that includes a near-field region (associated with shorter ranges) and a far-field region (associated with longer ranges). The image in both the near and the far-field regions is formed with the same imaging mode such as B-mode or M-mode imaging. The image in the near-field region is modulated primarily in response to echo information in a harmonic frequency band, while the far-field region is modulated primarily in response to echo information in the fundamental frequency band. In this way, echo information in both frequency bands is combined to produce an improved composite image.

DETAILED DESCRIPTION OF THE PRESENTLY PREFERRED EMBODIMENTS

Figure 1:
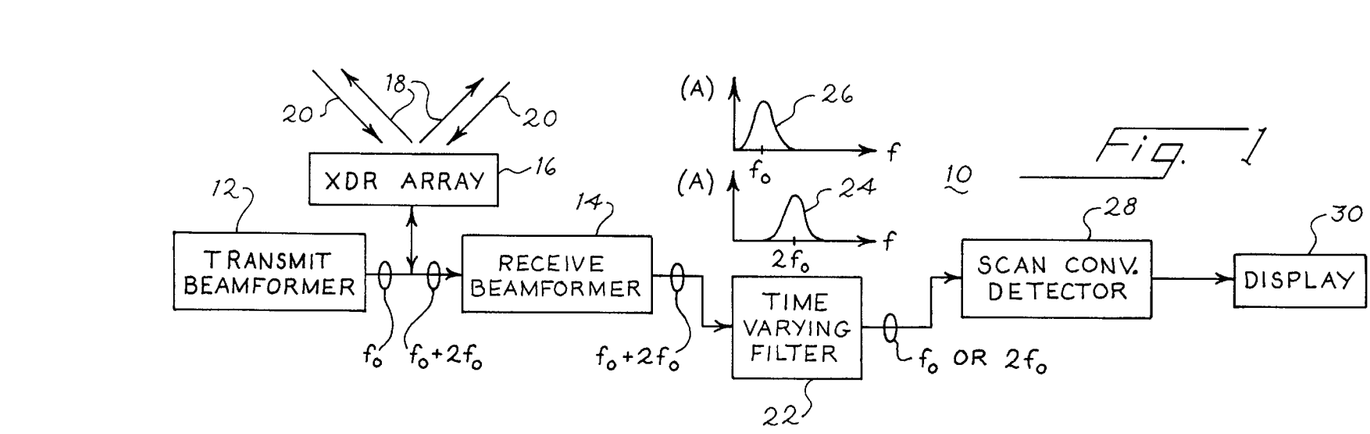
FIG. 1 is a block diagram of an ultrasound imaging system suitable for use with this invention.

Turning now to the drawings, FIG. 1 is a block diagram of an ultrasound imaging system 10 that incorporates a presently preferred embodiment of this invention. The system 10 includes a transmit beamformer 12 and a receive beamformer 14. These beamformers can take any desired form, either analog or digital, and they function generally in the conventional manner. In particular, the transmit beamformer generates transmit waveforms that are applied to a transducer array 16, which converts these transmit waveforms into ultrasonic energy that is directed along transmit beams 18 into a target, such as the body of a medical patient. Scattering sites within the target cause echo information to be returned to the transducer array 16. This echo information is converted by the transducer array 16 into electrical signals that are applied to the receive beamformer 14. The receive beamformer applies appropriate delays to form receive beams 20 in the conventional manner.

In this embodiment the transmit waveforms generated by the transmit beamformer 12 are characterized by a peak power level near a fundamental frequency $f_0$ (such as 2.5 MHz for example). The transmit waveforms are shaped to suppress transmitted ultrasonic energy at frequencies near a harmonic of the fundamental frequency. The ultrasonic echo information applied to the receive beamformer 14 will include echo information at the fundamental frequency band as well as echo information at a harmonic of the fundamental frequency band. In the following examples the harmonic of interest will be assumed to be the second harmonic ($2f_0$), though it should be understood that this invention can be applied generally to any suitable harmonic of the fundamental, including subharmonics and fractional harmonics. Of course, in the event that fundamental center frequency $f_0$ is changed, the center frequency of the corresponding harmonics will change as well.

In the embodiment of FIG. 1 the receive beamformer 14 generates receive beams that are applied to a time varying filter 22. As shown in FIG. 1 the receive beams applied to the time varying filter 22 include ultrasonic echo information at both the fundamental and the harmonic frequency bands. As shown in FIG. 1, the time varying filter 22 is controlled such that the passband of the filter 22 changes with time. The passband of the filter 22 is centered at the harmonic frequency $2f_0$ at shorter ranges along a given receive beam, and at the fundamental frequency $f_0$ for larger ranges of the same receive beam. This is schematically shown in the two curves of FIG. 1. The curve 24 shows the passband at shorter ranges along each receive beam, and the curve 26 shows the passband of filter 22 for longer ranges. Thus, the output of the time varying filter 22 is substantially restricted to fundamental components of the received echo information at longer ranges and to harmonic components of the received echo information for shorter ranges. The filtered output of the filter 22 is applied to a conventional scan converter and detector system 28, which provides image data for display on a display 30.

Figure 2:
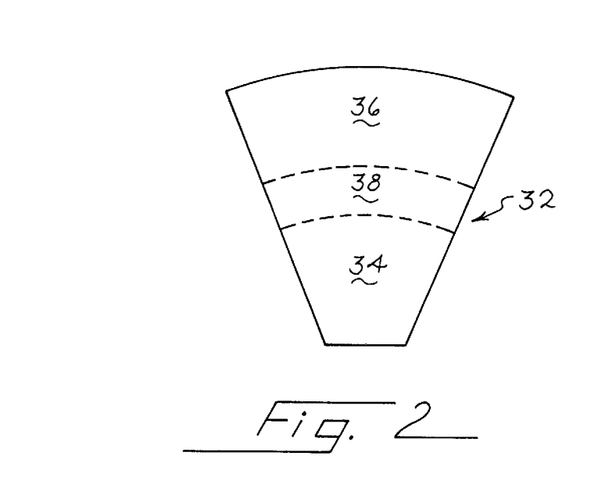
FIG. 2 is a schematic diagram of a composite image produced by the imaging system of FIG. 1.

FIG. 2 shows an example of the resulting composite image 32 displayed on the display 30. This composite image is characterized by a near-field region 34, a far-field region 36, and an intermediate region 38 situated between the near and far-field regions 34, 36. It should be understood that the terms near-field and far-field are not intended to define any specific ranges. Rather, the key characteristic is that the near-field region is associated with shorter ranges than the far-field region 36. As shown in FIG. 2, the near-field region 34 is spatially distinct from the far-field region 36, and both regions 34, 36 are formed using a common imaging mode. For example, all three of the regions 34, 36, 38 may be formed as B-mode image regions, M-mode image regions, or color Doppler image regions.

Because the time varying filter 22 selectively passes echo information centered at the harmonic frequency $2f_0$ for shorter ranges while blocking returning echo information centered at the fundamental frequency $f_0$, the near-field region 34 emphasizes and is primarily modulated in response to received ultrasonic echo information in the harmonic frequency band. Similarly, since the time varying filter 22 passes echo information centered at the fundamental frequency $f_0$ and blocks echo information centered at the harmonic frequency $2f_0$ for longer ranges of each receive beam, the far-field region 36 emphasizes and is primarily modulated in response to echo information in the fundamental frequency band. By way of example, the near-field region 34 may be modulated primarily in response to echo information at ultrasonic frequencies greater than 3 MHz, while the far-field may be modulated primarily in response to echo information at frequencies less than 3 MHz. In this way the imaging benefits of harmonic imaging are obtained for the near-field 34, where they are most useful, while the penetration advantages of fundamental imaging are obtained for the far-field.

Figure 3:
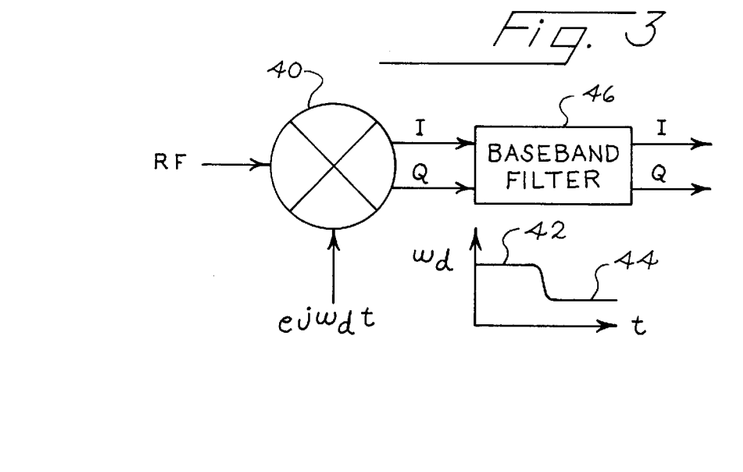
FIG. 3 is a schematic diagram of an alternate filtering approach suitable for use in the system of FIG. 1.

In the embodiment of FIG. 3, the time varying filter is implemented using demodulation techniques. In particular, a broadband RF signal is applied to a multiplier 40 that also receives a demodulation signal. This demodulation signal is characterized by a demodulation frequency as shown at 42. The demodulation frequency shifts from a higher frequency at shorter ranges along each receive beam (appropriate for emphasizing the harmonic component of the broadband receive signal) to a lower frequency for longer ranges along each receive beam (appropriate for demodulating the fundamental component of the received echo information). The output of the multiplier 40 is in the I.Q. format and is applied to a baseband filter 46. Thus, the multiplier 40 operates to mix the broadband receive signal with a sinusoidal signal having a time varying center frequency. Initially during each receive beam it is the harmonic component of the receive signal that is centered at 0 Hz and at longer ranges of each receive beam it is the fundamental frequency that is centered at 0 Hz. The lowpass filter 46 removes components at higher frequencies, thereby substantially eliminating the fundamental frequency components at shorter ranges and the harmonic frequency components at longer ranges.

Time varying passband filters are used in other ultrasonic imaging applications as discussed in U.S. Pat. Nos. 4,016,760 and 5,218,869 and in U.S. patent application Ser. No. 08/432,615, filed May 2, 1995, assigned to the assignee of the present invention.

Figures 4, 5:
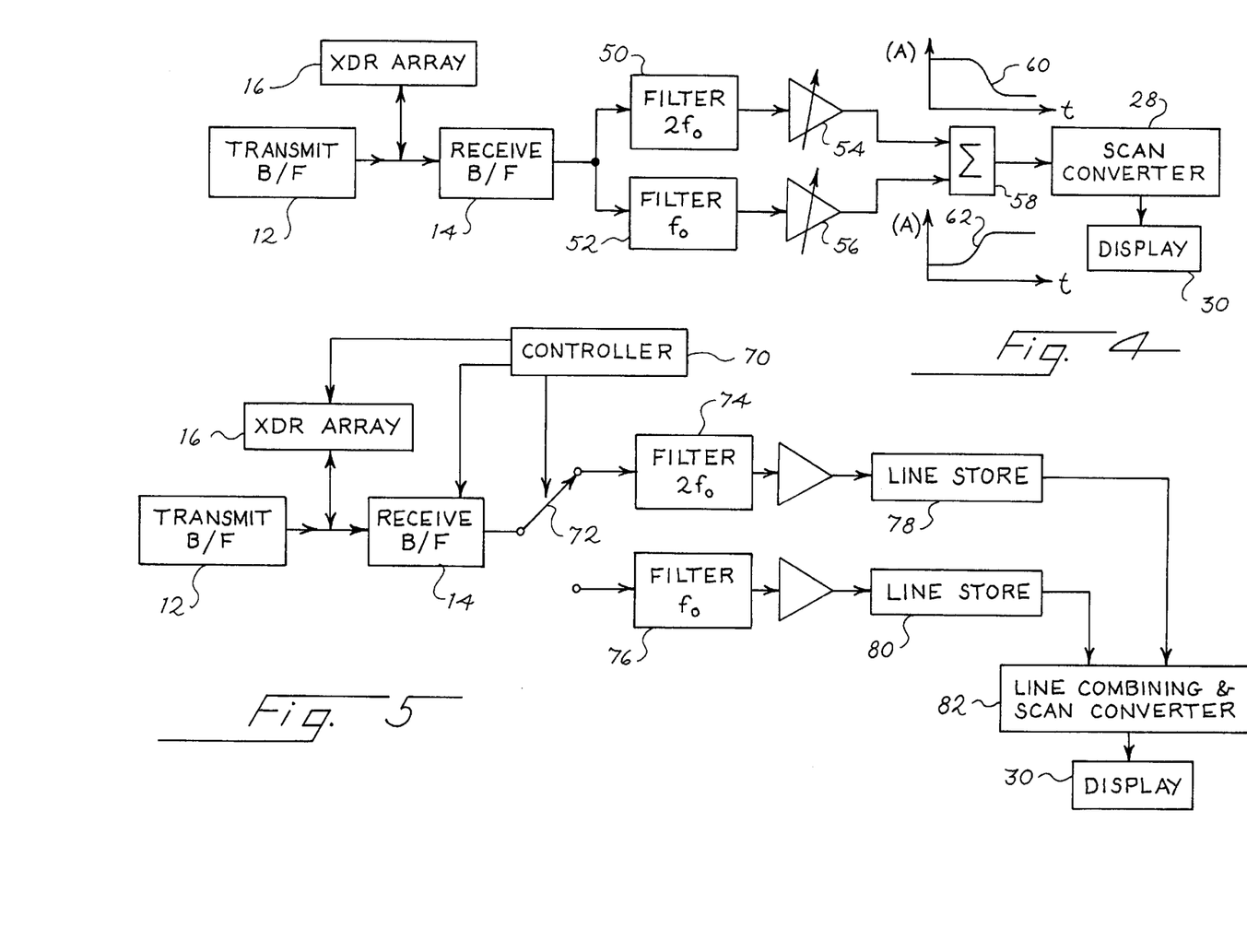
FIGS. 4 and 5 are block diagrams of alternate embodiments of ultrasonic imaging systems suitable for use with this invention.

FIG. 4 shows another embodiment in which the echo ultrasound information supplied by the receive beamformer is applied to two bandpass filters 50, 52. The bandpass filter 50 passes the harmonic component of the received ultrasonic energy while blocking the fundamental component, and the filter 52 passes the fundamental component of the received ultrasonic energy while blocking the harmonic component. The filtered outputs of the filters 50, 52 are applied to time varying gain amplifiers 54, 56, and the outputs of the amplifiers 54, 56 are applied to a summer 58. The curves 60, 62 show the time varying gains applied by the amplifiers 54, 56. Note that the amplifier 54 initially has a high amplitude which falls for longer ranges along each receive beam, while the amplifier 56 initially provides low amplitude amplification which rises for longer ranges along each receive beam. In this way the harmonic component of the received echo information is emphasized at near-field portions of each receive beam and the fundamental component is emphasized at far-field portions of each receive beam.

The approach described above in conjunction with FIG. 4 can be implemented using demodulators for the filters 50, 52 to emphasize respective passbands of the broadband receive signal. As used herein, the harmonic and fundamental components of the received ultrasonic energy correspond to signals which are responsive to the components in the harmonic and fundamental ultrasonic passbands when in the acoustic domain, respectively. For this reason, the harmonic and fundamental components may be processed either as RF signals with typical frequencies of 2–20 MHz or as baseband signals with frequencies near 0 Hz.

Any suitable technique can be used to isolate the harmonic and fundamental components in the received signals. In addition to the demodulation techniques and the filters described above, filters can be used before the received signals are applied to the receive beamformer, and alternate channel phasing techniques can be used. All such approaches are encompassed within the term "filter means."

It is not essential in all embodiments that both the fundamental and the harmonic components for the image be obtained from a single firing or transmit event. In the system shown in FIG. 5 a controller 70 controls the transmit and receive beamformers 12, 14 and a switch 72 such that two or more transmit beams are fired for each beam direction (i.e., two or more transmit events for each beam direction). The respective receive beams are analyzed separately. For example, the controller 70 can position the switch 72 such that one of each set of receive beams is processed by the filter 74 and then stored in the line store 78, while another receive beam within each set is directed to the filter 76 and stored in the line store 80. In this embodiment the filter 76 is a passband filter that is centered at the fundamental frequency $f_0$, while the filter 74 is a passband filter that is centered at the harmonic frequency $2f_0$. The scan converter 82 selects appropriate portions of the information stored in the stores 78, 80 to create the near-field and far-field regions as described above. Although not shown in FIG. 5, the filters 74, 76 could be replaced with a single filter with switchable components. Also, if the receive signals are filtered prior to beamforming, the beamformer can be made to operate in a narrower band of operation, which may be less expensive to implement.

The depth and associated time at which the transition from harmonic to fundamental imaging is made is best determined from experimentation, and will vary based on the frequencies and the transducers being used. As the system makes a transition from harmonic imaging in the near-field to fundamental imaging in the far-field a significant change (increase) in apparent signal level will appear due to the reduced attenuation of the fundamental component. In order to avoid a bright region appearing in the image at the far-field, it is preferred to apply depth dependent gain to the signals to make the image more uniform. In some respect, this use of depth dependent gains is similar to focal gain compensation, and manually controlled depth gain controls well known to those skilled in the art.

Figure 6A:
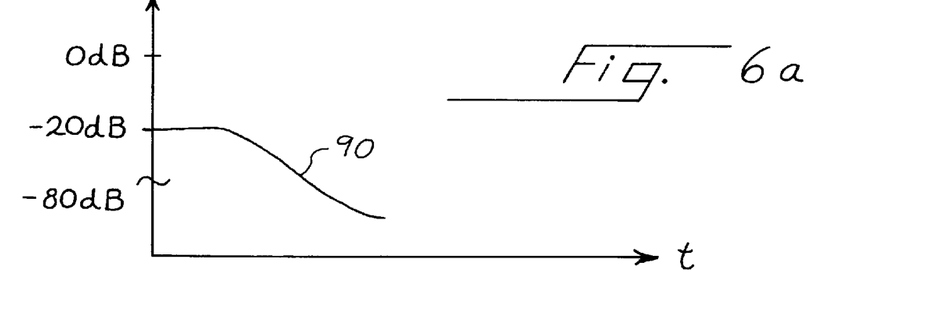
FIGS. 6A–6E are graphs showing exemplary amplitude and amplification factor curves.
Figure 6B:
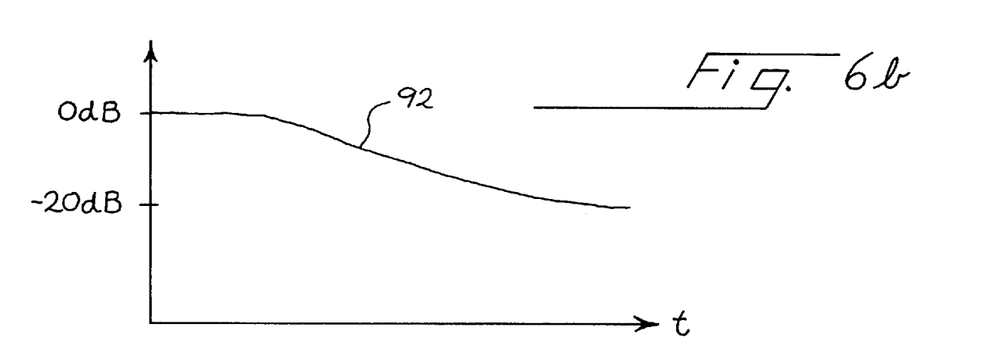

Either during the scan conversion process or in an earlier stage in signal processing, signal gains are preferably matched so that the composite image has an appropriate brightness/darkness balance between the near-field and the far-field. This is schematically shown in FIGS. 6A–6E. The horizontal axis in the graphs of FIGS. 6A–6E is time, with the left-hand region of the horizontal axis corresponding to the near-field region and the right-hand region of the horizontal axis corresponding to the far-field region. FIGS. 6A and 6B show the expected signal level as a function of time for the harmonic and the fundamental components of the received echo information, respectively. As shown in FIGS. 6A and 6B, the intensity of the fundamental component is substantially greater than that of the harmonic component in the far-field.

Figure 6C:
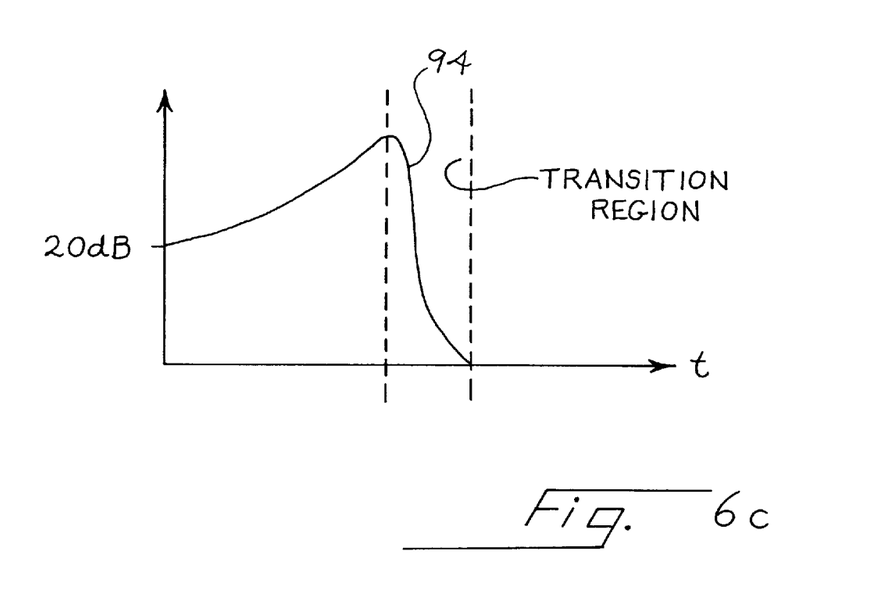
Figure 6D:
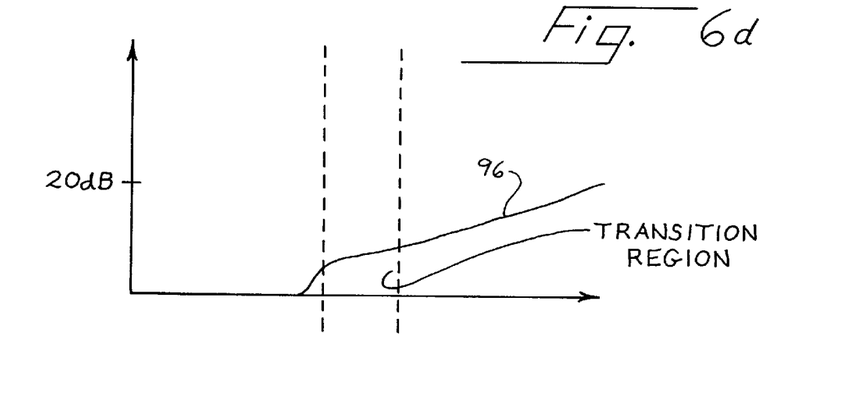
Figure 6E:
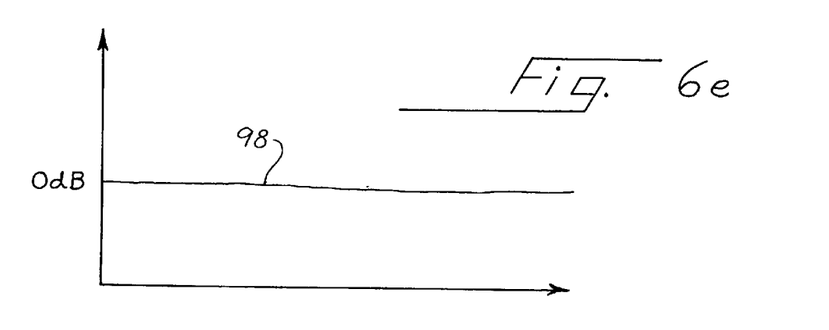

FIG. 6C shows appropriate gains that can be used on the harmonic component. Note that the gain starts at a relatively high level, increases to a point at the mid range, and then falls abruptly. FIG. 6D shows a comparable gain function as adapted for the fundamental component. This gain function starts at a very low level, increases sharply at the mid range, and then continues to increase gradually. In operation, any of the systems described above in effect multiplies the curve 90 with the curve 94 to provide a desired range-independent amplitude for the harmonic component in the near-field, and then multiplies the curves 92 and 96 to provide a matched amplitude, range-independent amplitude for the fundamental component in the far-field. Thus, the product of curves 90 and 94 summed with the product of curves 92, 96 produces the desired balanced amplitude curve 98 of FIG. 6E.

Figure 7:
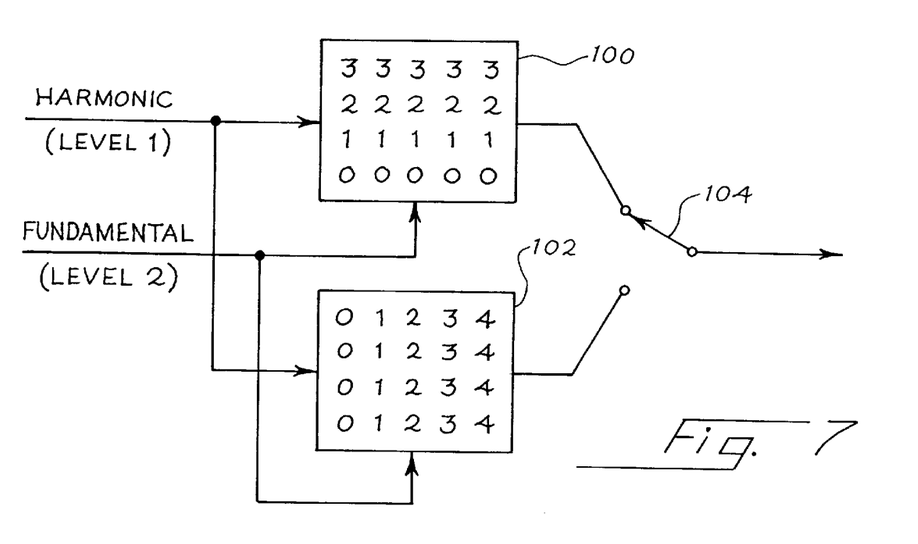
FIG. 7 is a block diagram of another filtering system suitable for use with this invention.

The desired depth dependent amplitude changes can be implemented in many ways, including the automatic gain compensation technique described in U.S. Pat. No. 5,579,768, assigned to the assignee of the present invention, or by using nonlinear methods for combining the harmonic and the fundamental components. Such nonlinear techniques may include the use of look up tables 100, 102 as shown in FIG. 7. The look up tables 100, 102 receive both the harmonic and the fundamental components as inputs. These components may be generated in any of the ways described above, or in other ways known to those skilled in the art. The look up table 100 stores amplitude values suitable for use in the near-field, and the look up table 102 stores amplitude values suitable for use in the far-field. A switch 104 is controlled to select the look up table 100 for near-field portions of the image and the look up table 102 for far-field portions of the image. As shown in the example of FIG. 7, in the event the harmonic component has a level equal to 1 and the fundamental component has a level equal to 2, the look up table 100 provides an output amplitude of 1 during near-field operation while the look-up table 102 provides an amplitude of 2 during far-field operation. Of course, more than two look up tables can be provided, and if desired the look up table may be changed for example every 5 millimeters of depth.

In the intermediate region of FIG. 2, a mixture of the fundamental and harmonic components will be displayed. The proportion of the contribution of each of these components, as functions of depth, can best be determined from experimental observation.

As yet another alternative implementation, it is possible to duplicate all or essentially all of the components of the receive beamforming hardware, and then to sum the fundamental and harmonic components after duplicate processing. As an example, the receive beamformer may be duplicated, and signal mixing can be performed in the scan conversion stage. It is anticipated that the duplication of hardware, though technically feasible, will in many applications increase the overall cost of the system.

The imaging depth at which any of the systems described above switch from emphasizing the harmonic component to emphasizing the fundamental component in the resulting composite image can be made automatic. For example, if the mean signal level of the harmonic component falls below a known noise limit of the imaging system (such as −80 dB) an automatic control system can be provided to automatically switch from fundamental to harmonic imaging. Similarly, the appearance of speckle flashing between successive lines can be used as a criterion. Speckle may be detected by cross correlating successive lines and detecting a lack of correlation in the far field. A rapid speckle effect is typically attributed to electrical noise, and when this component becomes significant it is generally preferable to switch from harmonic imaging to fundamental imaging.

The systems described above provide the important advantage that optimal detail and contrast resolution are provided in the near-field, without sacrificing overall penetration performance in the far-field.

It is not essential in all embodiments of this invention that the near-field region of the composite image emphasize only the harmonic component. If desired, the near-field region may represent an amplitude-matched combination of the fundamental and harmonic signals. For example, the fundamental and harmonic image signals may be processed via separate signal paths in parallel, or by means of sequential operation using successive fundamental and harmonic modes along the same beam direction. The resulting fundamental and harmonic image data is subjected to depth dependent gain adjustment so as to form two amplitude-matched image data sets capable of producing approximately uniform images. These two images (one at the fundamental band and the other at the harmonic band) are then summed or averaged to produce a frequency compounded image for the near-field region. In the far-field region, at ranges where the harmonic signal is near the noise level, the fundamental signal is used in the composite image as discussed above.

The well known advantage of a frequency compounded image is that coherent speckle effects are reduced, while signal components associated with tissue structure are summed. This results in an image which has a contrast characteristic that allows regions of slightly differing back scatter intensity to be more easily differentiated.

The intensity correction method used to produce amplitude-matched images of the fundamental and harmonic components may be based on the circuit disclosed in Klesenski U.S. Pat. No. 5,579,768, assigned to the assignee of the present invention, or any suitable alternative approach. For example, the variations of gain may be estimated and a stored compensation function applied to the beamform signals. Alternately, carefully chosen filter characteristics may be used so that both the fundamental and harmonic components are approximately equalized in amplitude in the raw input signal form. In this case the compounding may be achieved at the final stage when the signals are detected prior to image display.

In order to obtain the advantages of frequency compounding, it is important that the amplitudes of the harmonic and fundamental signals be matched. As used herein, matched amplitude refers to mean pixel amplitudes that are substantially equal to one another by a factor of plus or minus 50% over an image region such as a substantially constant range band. More preferably, matched amplitudes are equal to one another across a region of the image by plus or minus 25%, and most preferably by plus or minus 10%.

As in the preceding embodiments, in the far-field region, where there is insufficient energy in the harmonic component, the system switches using any of the techniques described above such that the far-field is modulated primarily in response to the fundmental component.

As another alternative, ultrasonic energy may be transmitted in any of the foregoing embodiments in different transmit events, including a first transmit event focused at a greater depth and a second transmit event focused at a lesser depth along the same beam direction. Preferably the peak power level of the first transmit event is positioned at a higher frequency than the peak power level of the second transmit event. For example, the first and second transmit events may be associated with respective first and second transmit zones that meet at a zone boundary. The peak power levels of the first and second transmit events are preferably positioned in frequency such that the fundamental frequency band associated with the first transmit event and the harmonic frequency band associated with the second transmit event are substantially matched in frequency at the zone boundary.

For example, in the case where multiple transmit zones are used, the closer zone or zones may be imaged using the harmonic component (e.g. transmit at 2 MHz and receive at 4 MHz). As a result of depth and frequency dependent attenuation, the center of the received harmonic component at the zone boundary may be 3.5 MHz, slightly less than the 4 MHz frequency characteristic of the inner edge of the first zone. For the next transmit zone at greater depths the fundamental component is used for imaging. In this case, the transmit frequency may be between 2 and 3.5 MHz. Ideally, the center transmit frequency for the longer range zone is chosen so that the fundamental component at the zone boundary matches the harmonic component of the shorter range zone at the zone boundary (i.e. 3.5 MHz). In this way a well matched spatial resolution is obtained at the zone boundary, and system requirements in terms of mixing fundamental and harmonic signal components are simplified.

Preferably, the image components for the near-field and far-field regions are gain matched as a function of depth to minimize brightness banding. Systems for splicing the responses of adjacent transmit zones with minimal artifactual seams are disclosed in Finger U.S. Pat. No. 5,579,770, assigned to the assignee of the present invention. The embodiment of FIG. 5 described above can be adapted for operation in the mode described above. In this case, the transmit beamformer is preferably of the type described in U.S. patent application Ser. No. 08/673,410, filed Jul. 15, 1996 and assigned to the assignee of the present invention.

The foregoing detailed description has described only a few of the many forms that the present invention can take. Those skilled in the art will recognize that many alternatives are possible. For example, a broadband receive signal can be used for forming the far-field image, since the relative contribution of the harmonic signal component is small as compared to the fundamental frequency component in the far-field. Also, the present invention can be used for tissue harmonic imaging (where no added non-linear contrast agent is introduced into the patient during an entire ultrasound examination session) and for harmonic imaging which utilizes added non-linear contrast It is therefore only the following claims, including all equivalents, that are intended to define the scope of this invention.

What is claimed is:

1. An ultrasonic imaging method comprising:
   (a) transmitting ultrasonic energy into a target, said ultrasonic energy characterized by a peak power level near a fundamental frequency band;
   (b) receiving ultrasonic echo information associated with said transmitted ultrasonic energy in first and second frequency bands, said first frequency band comprising said fundamental frequency band, said second frequency band comprising a harmonic of said fundamental frequency band and substantially excluding said fundamental frequency band;
   (c) forming a composite image in response to said received ultrasonic echo information, said composite image comprising spatially distinct near-field and far-field regions, said far-field region emphasizing echo information in the first frequency band and said near-field region emphasizing echo information in the second band.

2. An ultrasonic imaging method comprising:
   (a) transmitting ultrasonic energy into a target, said ultrasonic energy characterized by a peak power level near a fundamental frequency band;
   (b) receiving ultrasonic echo information associated with said transmitted ultrasonic energy in first and second frequency bands, said first frequency band comprising said fundamental frequency band, said second frequency band comprising a harmonic of said fundamental frequency band and substantially excluding said fundamental frequency band;
   (c) forming a composite image in response to said received ultrasonic echo information, said composite image comprising spatially distinct near-field and far-field regions, said far-field region emphasizing echo information in the first frequency band and said near-field region emphasizing an amplitude-matched combination of echo information in the first and second bands.

3. The method of claim 1 or 2 wherein the near-field region and the far-field region are displayed in a common imaging mode.

4. The method of claim 1 or 2 wherein (b) comprises receiving ultrasonic echo information associated with multiple transmit events, such that the first and second frequency bands are associated with different transmit events.

5. The method of claim 1 or 2 wherein (b) comprises receiving energy in the first and second frequency bands in association with a common transmit event.

6. The method of claim 4 wherein (a) comprises transmitting said ultrasonic energy into the target in said different transmit events, wherein said different transmit events comprise a first transmit event focused at a greater depth and a second transmit event focused at a lesser depth.

7. The method of claim 6 wherein the peak power level of the first transmit event is at a higher frequency than the peak power level of the second transmit event.

8. The method of claim 7 wherein first and second transmit events are associated with respective first and second transmit zones that meet at a zone boundary, and wherein the peak power levels of the first and second transmit events are positioned in frequency such that the first frequency band associated with the first transmit event and the second frequency band associated with the second transmit event are substantially matched in frequency at the zone boundary.

9. A composite diagnostic medical ultrasonic image comprising:

a near-field image portion and a far-field image portion;
said far-field image portion modulated primarily in response to received ultrasound echo information in a fundamental frequency band;
said near-field image portion modulated primarily in response to received ultrasound echo information at a harmonic of the fundamental frequency band.

10. The invention of claim 9 wherein both said image portions are displayed in a common imaging mode.

11. A composite diagnostic medical ultrasonic image comprising:
a near-field image portion and a far-field image portion;
said far-field image portion modulated primarily in response to received ultrasonic echo information characterized by an ultrasonic frequency less than X MHz;
said near-field image portion modulated primarily in response to received ultrasonic echo information characterized by an ultrasonic frequency greater than X MHz.

12. The invention of claim 11 wherein X=3.

13. The invention of claim 11 wherein both said image portions are displayed in a common imaging mode.

14. An ultrasonic imaging system comprising:
transmit beamformer means for forming a plurality of ultrasonic transmit beams at a fundamental frequency band;
an ultrasonic receiver comprising a receive beamformer and means for filtering received signals to form a fundamental component and a harmonic component;
means for forming an image in response to the fundamental and harmonic components, said image comprising a near-field region responsive primarily to the harmonic component and a far-field region responsive primarily to the fundamental component.

15. An ultrasonic imaging system comprising:
transmit beamformer means for forming a plurality of ultrasonic transmit beams at a fundamental frequency band;
an ultrasonic receiver comprising a receive beamformer and means for filtering the received signals to form a fundamental component and a harmonic component;
means for forming an image in response to the fundamental and harmonic components, said image comprising a near-field region responsive primarily to an amplitude-matched combination of the harmonic component and the fundamental component and a far-field region responsive primarily to the fundamental component.

16. The invention of claim 14 or 15 wherein both of said regions are formed in a common imaging mode.

17. The invention of claim 14 or 15 wherein the filtering means forms the fundamental and harmonic components from separate transmit events.

18. The invention of claim 14 or 15 wherein the filtering means forms the fundamental and harmonic components from a common transmit event.

19. The invention of claim 14 wherein the filtering means comprises a time varying filter which passes the harmonic component of near-field portions of the receive beams and the fundamental component of far-field portions of the receive beams.

20. The invention of claim 14 wherein the filtering means comprises a time varying demodulator that demodulates the harmonic component of near-field portions of the receive beams and the fundamental component of far-field portions of the receive beams.

21. The invention of claim 14 wherein the filtering means comprises:
first and second filters operative to selectively pass the fundamental and harmonic components, respectively, of the receive beams; and
first and second time varying amplifiers responsive to the first and second filters, respectively; and
a summer responsive to the first and second time-varying amplifiers.

22. The invention of claim 14 wherein the filtering means comprises:
first and second filters operative to selectively pass the fundamental and harmonic components, respectively, of the receive beams; and
a switch coupled to the first and second filters to select a selectable one of the first and second filters.

23. The invention of claim 14 wherein the image forming means comprises:
an image processor;
a first and second look up table, each look up table responsive to both of the fundamental and harmonic components to generate a respective output signal; and
a switch operative to direct a selectable one of the output signals to the image processor.

24. The invention of claim 14 or 15 wherein one of the filtering means and the image forming means comprises means for balancing intensity in the near-field and the far-field regions.

25. The invention of claim 14 or 15 wherein the image forming means comprises means for automatically selecting an upper range limit for the near-field region in response to the harmonic component.

26. The invention of claim 14 or 15 wherein the image forming means comprises means for automatically selecting an upper range limit for the near-field region in response to an image quality parameter of the near-field region.

27. The invention of claim 15 wherein the harmonic and fundamental components are amplitude matched to within 50% of each other in the amplitude matched combination.

28. The invention of claim 15 wherein the harmonic and fundamental components are amplitude matched to within 25% of each other in the amplitude matched combination.

29. The invention of claim 15 wherein the harmonic and fundamental components are amplitude matched to within 10% of each other in the amplitude matched combination.

30. An ultrasonic method for generating data for imaging comprising:
(a) transmitting ultrasonic energy at a fundamental frequency;
(b) focusing the ultrasonic energy to at least first and second depths;
(c) receiving ultrasonic echo information at a harmonic of the fundamental frequency and at the fundamental frequency; and
(d) compounding the ultrasonic echo information associated with the fundamental frequency with the ultrasonic echo information associated with the harmonic frequency.

31. The method of claim 30 wherein (d) comprises averaging the ultrasonic echo information associated with the fundamental frequency with the ultrasonic echo information associated with the harmonic frequency.

32. The method of claim 30 further comprising (e) generating an image responsive to (d) and associated with reduced speckle.

33. The method of claim 30 wherein (d) comprises inputting the ultrasonic echo information associated with the fundamental frequency and the ultrasonic echo information associated with the harmonic frequency into a look-up table.

34. The method of claim 30 wherein the ultrasonic echo information associated with the fundamental frequency and the ultrasonic echo information associated with the harmonic frequency comprise detected data.

35. The method of claim 30 wherein the ultrasonic echo information associated with the fundamental frequency and the ultrasonic echo information associated with the harmonic frequency comprise RF data.

36. The method of claim 30 wherein (a) comprises transmitting the ultrasonic energy in first and second transmit events for the first and second depths, respectively.

37. The method of claim 32 wherein (e) comprises generating the image for a near-field region of a display.

38. The method of claim 30 wherein (d) comprises amplitude matching the echo information associated with the fundamental frequency and the echo information associated with the harmonic frequency prior to compounding.

39. The method of claim 30 wherein (d) comprises amplitude matching the echo information associated with the fundamental frequency and the echo information associated with the harmonic frequency to within 50% prior to compounding.

40. The method of claim 30 wherein (d) comprises amplitude matching the echo information associated with the fundamental frequency and the echo information associated with the harmonic frequency to within 25% prior to compounding.

41. The method of claim 30 wherein (d) comprises amplitude matching the echo information associated with the fundamental frequency and the echo information associated with the harmonic frequency to within 10% prior to compounding.

* * * * *

UNITED STATES PATENT AND TRADEMARK OFFICE
CERTIFICATE OF CORRECTION

PATENT NO. : 6,132,374
DATED : October 17, 2000
INVENTOR(S) : John A. Hossack et al.

It is certified that error appears in the above-identified patent and that said Letters Patent is hereby corrected as shown below:

Title page,
Under "OTHER PUBLICATIONS",
Line 2, delete "*Ulatrason*" and substitute -- *Ultrason* -- in its place.
Line 18, delete "11/26/11996" and substitute -- 11/26/1996 -- in its place.

Column 7,
Line 63, insert -- agent. -- after "contrast".

Signed and Sealed this

Second Day of April, 2002

Attest:

Attesting Officer

JAMES E. ROGAN
Director of the United States Patent and Trademark Office